(12) United States Patent
Pasternack et al.

(10) Patent No.: US 9,260,680 B2
(45) Date of Patent: Feb. 16, 2016

(54) PROLAMIN-REDUCED BEVERAGES AND METHODS FOR THE PREPARATION THEREOF

(75) Inventors: Ralf Pasternack, Griesheim (DE); Stefan Marx, Rossdorf (DE); Dominik Jordan, Darmstadt (DE)

(73) Assignee: N-Zyme Biotech GmbH, Darmstadt (DE)

( * ) Notice: Subject to any disclaimer, the term of this patent is extended or adjusted under 35 U.S.C. 154(b) by 1120 days.

(21) Appl. No.: 11/666,718

(22) PCT Filed: Nov. 10, 2005

(86) PCT No.: PCT/EP2005/055881
§ 371 (c)(1),
(2), (4) Date: Sep. 11, 2007

(87) PCT Pub. No.: WO2006/051093
PCT Pub. Date: May 18, 2006

(65) Prior Publication Data
US 2008/0003327 A1    Jan. 3, 2008

Related U.S. Application Data

(60) Provisional application No. 60/626,760, filed on Nov. 11, 2004.

(30) Foreign Application Priority Data

Nov. 10, 2004    (EP) .................................... 04105672

(51) Int. Cl.
| | | |
|---|---|---|
| *A23L 2/84* | (2006.01) | |
| *C12C 5/00* | (2006.01) | |
| *A23L 1/015* | (2006.01) | |
| *A23L 1/30* | (2006.01) | |
| *C12C 12/00* | (2006.01) | |

(52) U.S. Cl.
CPC ............... *C12C 5/004* (2013.01); *A23L 1/0153* (2013.01); *A23L 1/3014* (2013.01); *A23L 2/84* (2013.01); *C12C 12/00* (2013.01); *C12Y 101/03005* (2013.01); *C12Y 110/03002* (2013.01); *C12Y 111/01007* (2013.01); *C12Y 114/18001* (2013.01); *C12Y 203/02013* (2013.01); *C12Y 503/04001* (2013.01)

(58) Field of Classification Search
CPC ....... A23L 1/0153; A23L 1/3014; A23L 2/84; C12C 5/004; C12C 12/00; C12Y 503/04001
USPC .............. 426/11, 14, 15, 16, 18, 590, 61, 592
See application file for complete search history.

(56) References Cited

U.S. PATENT DOCUMENTS

| | | | | |
|---|---|---|---|---|
| 6,106,887 | A | 8/2000 | Yamazaki et al. | ............. 426/622 |
| 2001/0041199 | A1 | 11/2001 | Davids | ............................ 426/11 |
| 2003/0157217 | A1* | 8/2003 | Schmedding et al. | ........... 426/12 |

FOREIGN PATENT DOCUMENTS

| | | | |
|---|---|---|---|
| DE | 10163964 | 7/2003 | ............... C12C 1/00 |
| EP | 0760209 | 3/1997 | ............... A21D 8/04 |
| EP | 0949329 | 10/1999 | ............. C12C 11/00 |
| EP | 1063285 | * 12/2000 | |
| EP | 1190624 | 3/2002 | ............... A21D 8/04 |
| EP | 1313375 | 5/2003 | ................. A23J 1/12 |
| JP | 4044071 | 4/1979 | ............... A23G 3/30 |
| JP | 10075716 | 3/1998 | ................. A23J 3/34 |
| JP | 10075716 A | * 3/1998 | |
| WO | 9521240 | 8/1995 | |
| WO | 9622366 | 7/1996 | |
| WO | 9729179 | 8/1997 | |
| WO | 9960200 | 11/1999 | |
| WO | 0070064 | 11/2000 | |
| WO | WO01/65948 | 9/2001 | ................. A23J 3/08 |
| WO | WO02/15713 | 2/2002 | ................. A23J 1/12 |
| WO | WO02/051873 | 8/2002 | ............... C08B 30/04 |
| WO | WO2006/051093 | 5/2006 | ............... C12C 5/00 |

OTHER PUBLICATIONS

International Search Report and Written Opinion dated Feb. 14, 2006 based on PCT application No. PCT/EP2005/055881.
Boyiu et al.;*Horseradish . . . w.β-Casein; J.Agric Food Chem*, v.52 No. 21; Sep. 25, 2004; p. 6633-6639.
Fink et al.; *γ-Glutamylamine . . . compounds; Proc.Natnl.Acad Sci* v.77, No. 8, pp. 4564-4568.
Folk et al.;ε-(γ-*Glutamyl*)*lysine crosslink*;Adv.Protein Chem 31; p. 1-133, (1977).
Seguro et al.; ε-(γ-*Glutamyl*)*lysine . . . Bound;J.Agric.Food.Chem* 1995 v.43; pp. 1977-1981.
Thalmann et al.; *Enzymatic . . . w. tyrosine; Euro Food Res Technol* 2002.
Yokoyama et al.;*Properties . . . transglutaminase;Appl.Microbiol Biotechnol* 2004 v.64:447-454.
International Search Report dated May 31, 2007.
Review of the National Starch and Chemical Company, "*Food Starch Techonlogy a Global Commitment*"; 1996; pp. 1-17.
Rasmussen et al.; "cDNA Cloning, Characterization and Expression of an Endosperm—Specific Barley Peroxidase"; Planet Molecular Biology; vol. 19 1991; pp. 317-327.
Rasmussen et al.; "Purification, Characterization and Stability of Barley Grain Peroxidase BP 1, A New Type of Plante Peroxidase"; Physiologia Plantarum; vol. 100 1997; pp. 102-110.
Interesse et al.; "Characterization of Wheat O-Diphenoise Isoenzyme"; Phytochemistry; vol. 22, No. 9 1993; pp. 1885-1889.
De Azevedo et al.; "Protein Disulphide-Isomerase of Mature and Developing Wheat"; 608th Meeting, Keele, 1984; pp. 1043.
Kunze, Wolfgang; "Technology Brewing and Malting"; VLB Berlin, Verlagsabteilung, 1996; pp. 81-87.
Notice of Opposition for European application No. 05810988.5.

* cited by examiner

*Primary Examiner* — Vera Stulii
(74) *Attorney, Agent, or Firm* — Ohlandt, Greeley, Ruggiero & Perle, LLP

(57) ABSTRACT

A process for the preparation of a beverage, a beverage base, a beverage concentrate or a beverage additive having a reduced prolamin content from prolamin-containing raw materials, comprising the following steps:
a) contacting the beverage or a precursor of the beverage with cross-linking enzymes to obtain modified prolamin;
b) removing the modified prolamin at least partially.

15 Claims, 3 Drawing Sheets

PROLAMIN-REDUCED BEVERAGES AND METHODS FOR THE PREPARATION THEREOF

CROSS-REFERENCED APPLICATIONS

This application is a 371 of International Application No. PCT/EP05/55881, filed on Nov. 10, 2005, and claims priority to U.S. Provisional Application No. 60/626,760, filed on Nov. 11, 2004, which is incorporated herein in its entirety by reference thereto.

The present invention relates to beverages having a reduced prolamin content and methods for the preparation thereof.

Prolamins (gluten) are a heterogeneous group of ethanol-soluble proteins from various cereal species and are referred to as gliadins in wheat, hordeins in barley, secalins in rye and avenins in oat. Despite of structural differences within the primary sequences, the prolamins are also frequently referred to generally as glutens or gliadins irrespective of whether they are derived from wheat or a different cereal species. A large number of cereal species employed in the food and beverage industries contain prolamins, in part in significant amounts. In an exemplary manner for the beverage industry, there may be mentioned: all types of beer and beer mix beverages, malt-based non-alcoholic beverages (e.g., malt beer), malt or cereal coffee. With a per capita annual consumption of about 80 liters, beer is still one of the most-consumed beverages in Europe. Alternatively, beer mix beverages and so-called innovative beverages with an additional benefit enjoy a growing popularity among the younger generation. For this reason and due to their high-value ingredients in terms of nutrition physiology, good market chances are predicted for beverages based on cereal raw materials. However, since all these beverages always contain prolamins (gluten) in various concentrations, the consumption of such beverages is strictly forbidden for celiac patients.

Celiac disease or sprue is a chronic auto-immune disease which is triggered by certain cereal proteins (prolamins, gluten) in genetically predisposed patients. In celiac patients, intestinal malabsorption syndromes due to extended lesions of the small intestine mucosa caused by the action of gluten occur mostly already in the first or second year of life. The vast majority of the patients express so-called HLA-DQ2 and/or HLA-DQ8 molecules. The current scientific view considers that the proliferation of T lymphocytes is induced by the interaction of specific gliadin molecules with HLA-DQ2/HLA-DQ8 antigens. This exceeding immune response is seen in a causal relationship with the degeneration of the small intestine mucosa. When the action of gluten continues, the epithelial regeneration becomes insufficient to cause atrophy of the villi of the small intestine and a reduced absorption performance, zero growth, dystrophy, muscular ionic deficiency, malodorous stool; there is even the possibility of malignant sarcomas. Further symptoms include depression and anemia.

Since currently no medicaments exist which result in a healing of sprue/celiac disease, the only possible therapy consists in a lifelong renunciation of gluten-containing foods. While an incidence rate of 1:1200 has been considered for the industrial nations in earlier years, an abundance of 1:100 to 1:200 is established today by extensive examinations and improved diagnostic possibilities, so that it can be considered that celiac disease is the most frequent chronic bowel disease in the Western population.

Dermatitis herpetiformis or Brocq-Duhring disease is a severely itching papulovesicular (papulae=nodules; vesicles=small blisters) dermatosis. Patients suffering from Brocq-Duhring disease also have celiac disease in up to 24% of the incidents, even though typical symptoms of the latter disease may often be lacking. In small intestine biopsies, even up to 85% of the dermatitis herpetiformis patients have alterations with variable villous atrophy typical of celiac disease. Accordingly, patients suffering from dermatitis herpetiformis Duhring should really be tested for celiac disease. In such cases, a gluten-free regimen mostly results in the disappearance of the skin lesions on a long-term basis.

In the selection and breeding of food cereals, a high protein and thus gluten content has long been sought for two reasons:

As compared to starch and other polysaccharides, protein is a more valuable component in terms of nutrition physiology, and gluten is critical for some technological properties in cereal processing. Thus, for example, the content and structure of gluten is critical for the essential physico-chemical properties, such as elasticity, gas-retaining property, tackiness or fermentation stability of doughs.

Therefore, in all important cereal species, such as wheat, rye, barley, but also spelt, unripe spelt grain, einkorn, emmer, kamut, triticale, bulgur and oat, prolamins are contained, which turn foods and beverages produced therefrom unfit for consumption by celiac patients.

When prolamin-containing cereal species are used for beverages, it is to be considered in most cases that gliadins are also present in the product, i.e., in amounts which preclude consumption by celiac patients. Both the use of gliadin-free cereals (buckwheat, rice, millet etc.) and a process control during the beverage production which ensures a general separation of proteins is mostly impossible for many reasons. In addition to the availability of the raw products, which is not always ensured, such beverages mostly also have altered organoleptic properties, such as taste or mouth feeling. Also, physico-chemical properties, such as foaming and foam stability, mostly do not reach those of traditional products, as expected by the consumers. Another problem is the risk of contamination of gliadin-free raw products/intermediate products with gliadin-containing raw products/intermediate products during production, shipping, storage and processing.

EP 0 949 329 A1 describes a gluten-free beer brewed from buckwheat and hydrolyzed corn starch using amylolytic enzymes and glucanase.

Alternatively, current research activities are directed to the development of genetically altered cereal varieties which are no longer able to produce gliadins. The developments are still in an early stage, and it is unpredictable currently whether and when these plants are cultured commercially, whether the raw materials obtained therefrom can further be employed for the brewing process, and what consumer acceptance such genetically modified cereal varieties will ultimately reach.

For this reason, almost all obtainable beverages on the basis of conventional cereal species contain detectable amounts of gliadins, and their content is particularly high in beers for the preparation of which barley or wheat is used.

Cross-linking enzymes are enzymes which can produce covalent bonds within proteins or between proteins and other substances, such as carbohydrates, phenols, and thus cause the formation of protein aggregates, sometimes with the participation of other substances. Typical representatives are transglutaminases, peroxidases, hexose-oxidases, tyrosinases and laccases, see also Thalmann C. R. & Lötzbeyer T. 2002: Enzymatic cross-linking of proteins with tyrosinase. Eur. Food Res. Technol. 214: 276-281; U.S. Pat. No. 6,358,543 (Method of improving the properties of a flour dough, a flour dough improving composition and improved food products), Boeriu C. G., Oudgenoeg G., Spekking W. T., Berendsen L. B., Vancon L., Boumans H., Gruppen H., van Berkel W. J., Laane C., Voragen A. G. 2004, Horseradish peroxidase-catalyzed cross-linking of feruloylated arabinoxylans with beta-casein. J. Agric. Food Chem., Oct. 20, 2004, 52(21): 6633-9.

Transglutaminases (protein-glutamine: amine-γ-glutamyltransferase; E.C. 2.3.2. 13) catalyze the building of stable cross-links between proteins. In this catalysis, the γ-carboxyamide function of glutamine side chains is transferred onto the ε-amino group of lysine residues with release of ammonium ions (Folk and Finlayson, Adv. Protein Chem. 31, 1-133 (1977)).

The isopeptide bond formed also withstands hydrolysis by proteases and is cleaved physiologically only after complete degradation of the proteins by γ-glutamylamine cyclotransferase and γ-glutamyltransferase (Fink et al., Proc. Natl. Acad. Sci. USA 77, 4564-4568 (1980), Seguro et al.; J. Agric. Food Chem. 43; 1977-1981 (1995)).

For technical applications, the bacterial transglutaminase of *Streptomyces mobaraensis* is suitable, in particular. The bacterial transglutaminase is derived from the non-pathogenic and non-toxic *Streptomyces mobaraensis*. By the American "Food and Drug Administration" (FDA), this TGase preparation was rated "generally regarded as safe" (GRAS) (GRN 000095). Due to its low-cost production, its broad range of substrates and its high reaction rates, this enzyme is destined for industrial applications in the food field. As examples, there may be mentioned: cross-linking of meat, fish, cheese, milk, whey proteins, soybean proteins and wheat proteins to achieve an improved structure, a higher viscosity or a comfortable mouth feeling. The design of new food products by the use of transglutaminase was enabled thereby (Yokoyama et al., Appl. Microbiol. Biotechnol. 64, 447-454 (2004)). WO 02/051873 describes a process for obtaining purified starch from protein-containing vegetable raw materials under the action of cross-linking agents, e.g., transglutaminase. After the proteins occurring in the raw material or additionally added have been cross-linked by transglutaminase, a facilitated separation of the starch from the protein network is possible.

EP 1 190 624 A2 describes methods for improving by means of transglutaminase the quality of low-wheat doughs in terms of baking technology. By employing the enzyme, an increased gas retaining property, a lower tackiness of the dough as well as an improved fermentation stability could be achieved, inter alia.

U.S. Pat. No. 6,106,887 discloses a process for the preparation of modified cereal flours by the use of transglutaminase during the make-up and/or milling process.

EP 0 760 209 A1 discloses the use of transglutaminase for the preparation of baking products having a multilayer structure.

WO 01/65948 discloses a protein preparation prepared under the action of transglutaminase from wheat protein (gluten) and whey protein and having improved technological properties, such as emulsifying property, gelling property or water binding property.

It was the object of the present invention to overcome the mentioned drawbacks and problems of the prior art, in particular, to provide a process for the preparation of prolamin-reduced beverages and related products.

This object is achieved by a process for the preparation of a beverage, a beverage base, a beverage concentrate or a beverage additive having a reduced prolamin content from prolamin-containing raw materials, comprising the following steps:

a) contacting the beverage or a precursor of the beverage with cross-linking enzymes to obtain modified prolamin;
b) removing the modified prolamin at least partially.

Suitable prolamin-containing raw materials include, in particular, wheat, cereals such as rye, oat, barley, spelt, unripe spelt grain, einkorn, emmer, triticale, bulgur, kamut or mixtures thereof.

Suitable cross-linking enzymes include, in particular, those from the enzyme classes of transglutaminases (EC 2.3.2.13), peroxidases (EC 1.11.1.7), hexose oxidases (EC 1.1.3.5), tyrosinases (EC 1.14.18.1), laccases (EC 1.10.3.2), protein disulfide isomerases (EC 5.3.4.1) and combinations thereof.

Particularly preferred cross-linking enzymes include bacterial transglutaminases, especially $Ca^{2+}$-independent transglutaminases from *Streptomyces mobaraensis*.

"Prolamins" within the meaning of this application include ethanol-soluble proteins from cereal species, which are also referred to as gluten, gliadins, hordeins, secalins or avenins.

"Beverage" means a food which can be ingested in a liquid form.

"Beverage base" or "beverage concentrate" means a precursor for the preparation of a food in solid or liquid form, which can be ingested as a food after further processing.

By the process according to the invention, the prolamin content in the beverages, beverage concentrates or beverage precursors can be reduced, wherein the physico-chemical properties of the beverage are altered as little as possible.

For example, the treatment with transglutaminase according to the invention can be used for the preparation of beers whose organoleptic and physico-chemical properties are like those of conventional beers. In particular, this applies to the foaming performance and foam stability, density, color, extract content, degree of fermentation or bitterness units.

The amount of enzyme to be employed depends on the enzyme preparation and may vary within wide limits. It depends on the prolamin content of the raw materials and intermediate products employed, the reaction time, the reaction temperature, pH value etc., as is known to those skilled in the handling of enzymes.

In the beverage preparation from cereals, especially in the preparation of beers, there are mostly process steps which enable the addition of the transglutaminase according to the invention without a high expenditure of time and cost. As a rule, these steps are followed by a heat-inactivation, filtration or centrifugation step, which enable the complete inactivation of enzyme activity and the at least partial separation of the modified prolamins.

According to the invention, beverages can be prepared which are selected from the group consisting of alcoholic beer, alcohol-reduced beer, non-alcoholic beer, malt beer, beer mix beverages, lemonades, soft drinks, fruit juice beverage, emulsion beverages, fruit juice mix beverages and mixtures thereof.

Within the scope of the process, proteins and protein hydrolysates approved for foods, such as gelatin, milk and whey proteins, may be added to the beverage of the precursor of the beverage before, during or after the contacting with the cross-linking enzymes.

For removing the modified prolamin, usual separation processes are suitable, such as filtration, centrifugation, sedimentation or sifting. Frequently, process steps from beverage production can be used simultaneously for the separation of the modified prolamin.

The enzymes may be employed in a purified form or in the form of a preparation, for example, an extract from a food-compatible organism.

In one embodiment, said contacting with cross-linking enzymes may be effected by adding microorganisms which recombinantly produce cross-linking enzymes. In particular, yeasts are suitable as said microorganisms. Alternatively, it is also possible that cross-linking enzymes are already being expressed in the cereals recombinantly and then come into contact with the prolamin within the scope of the process.

The selection of process conditions can be established by the skilled person in adaptation to the production process. The skilled person knows that the conversion rate of an enzyme reaction usually increases as the amount of enzymes or the temperature increases. Low temperatures require higher amounts or longer reaction times. At higher temperatures, smaller amounts or shorter times of action suffice.

Typically, the contacting with the beverage or the beverage precursor and the cross-linking enzymes is effected for a period of between 10 min and 24 hours. Typically, the temperature is between 5 and 50° C.

In one embodiment of the process, said contacting is followed by an inactivation step of the enzymes, especially a heat treatment.

The invention further relates to a beverage, beverage base, beverage concentrate or beverage additive obtainable by the process according to the invention, and a food which contains said beverage base or beverage concentrate, for example, in the form of a yogurt, a milk mix beverage, or a dietetic beverage with cereal contents, or a beverage powder.

According to the invention, the prolamin content of the beverage is reduced by the process. Preferably, the prolamin content after the treatment is below 500 ppm, more preferably below 100 ppm, still more preferably below 50 ppm, and most preferably below 20 ppm. Amounts of below 20 ppm are suitable for intake by celiac patients and dermatitis herpetiformis patients and can be considered "gluten-free".

The invention further relates to the use of cross-linking enzymes for the modification of prolamin in beverages, beverage bases or beverage concentrates made from prolamin-containing cereals.

The process according to the invention yields a beverage which due to its reduced prolamin content has a better tolerability for patients suffering from celiac disease and/or dermatitis herpetiformis. Surprisingly, the corresponding beverages also have improved physiological properties, especially in view of cloud stability (colloidal stability).

The invention is further illustrated by the following non-limiting Examples.

EXAMPLES

1) Determination of the Gliadin Content in Products

The analytical detection of gliadins in raw products, intermediate products and final beverages was effected with the RIDASCREEN® gliadin test, a sandwich enzyme immunoassay for the quantitative determination of gliadins from wheat and related prolamins from rye and barley in foods. With a detection limit of 1.5 ppm, this test kit currently represents the gold standard of analytical test systems.

Figure 1:
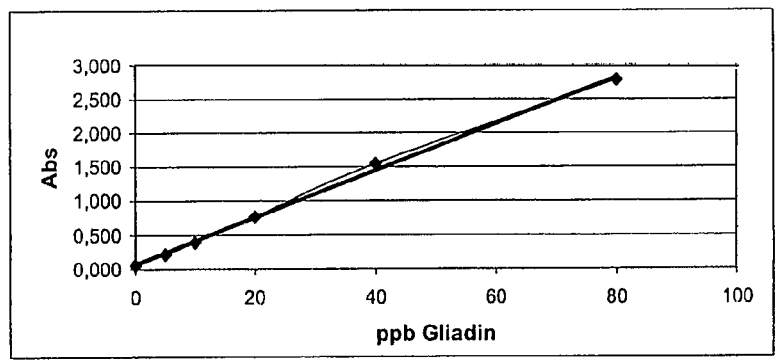
FIG. 1 shows a calibration straight line for determining the gliadin concentration in a sample.

The test principle is based on an antigen-antibody reaction. The wells of microtitration strips are coated with specific antibodies against gliadins. Upon addition of standard gliadin or a gliadin-containing sample, an antibody-antigen complex is formed which is recognized in a subsequent step by a second antibody to which the enzyme peroxidase is coupled. The detection is effected by adding urea peroxide substrate as well as a chromogen (tetramethylbenzidine). The enzyme bound to the antibody converts the colorless chromogen to a blue final product. The addition of a stop reagent ($H_2SO_4$) results in a color change from blue to yellow. The measurement is effected by photometry at 450 nm in a multititration plate reader. The gliadin concentration in μg/kg (ppb), which corresponds to the extinction of the sample, is read from the calibration curve, and the actual gluten content of the sample is calculated therefrom; cf. FIG. 1.

2) Removal of Gliadins from Weizenbier by Adding Transglutaminase

2a) Dependence on Enzyme Concentration

Figure 2A:
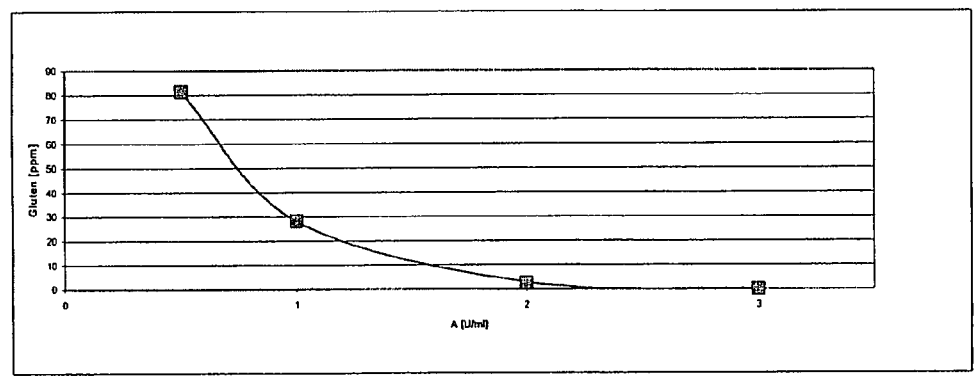
FIG. 2a shows the gluten reduction in Hefeweizen beer (2 hours, 37° C.) as a function of enzyme concentration.

In a 2 ml reaction vessel, 40 μl each of enzyme preparations with different transglutaminase activities was incubated with 1960 μl of beer at 37° C. for 2 h. After the lapse of the incubation time, the enzyme activity was inactivated for 10 min at 100° C. The gluten content of the solutions was determined by the process as described in Example 1. FIG. 2a shows the content of detectable gliadins as a function of enzyme concentration.

2b) Dependence on Incubation Time

Figure 2B:
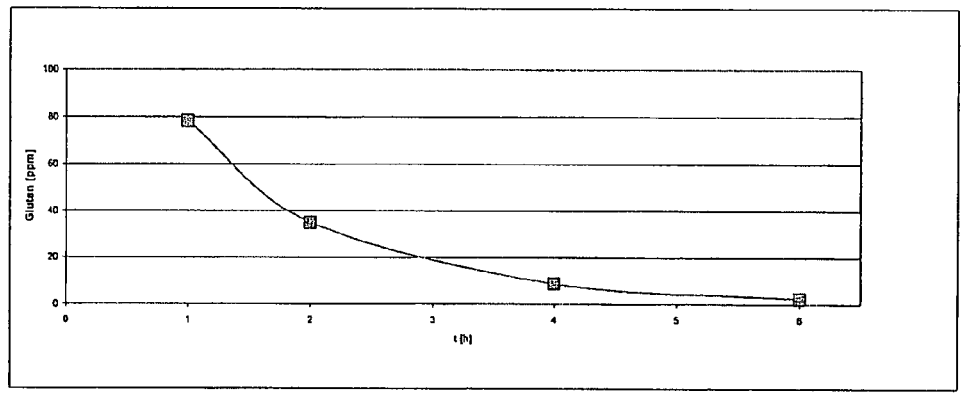
FIG. 2b shows the gluten reduction in Hefeweizen beer (1 U/ml, 37° C.) as a function of time.

In a 2 ml reaction vessel, 40 μl each of an enzyme preparation with a transglutaminase activity of 1 U/ml was incubated with 1960 μl of beer at 37° C. After the lapse of the incubation time, the enzyme activity was inactivated for 10 min at 100° C. The gluten content of the solutions was determined by the process as described in Example 1. FIG. 2b shows the content of detectable gliadins as a function of incubation time.

2c) Dependence on Temperature

Figure 2C:
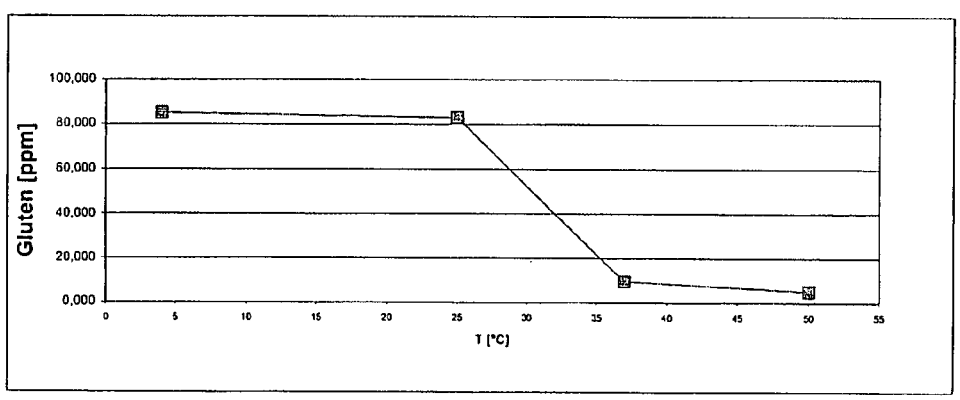
FIG. 2c shows the gluten reduction in Hefeweizen beer (25 U/ml, 2 hours) as a function of temperature.

In a 2 ml reaction vessel, 40 μl each of an enzyme preparation with a transglutaminase activity of 25 U/ml was incubated with 1960 μl of beer for 2 h at different temperatures. After the lapse of the incubation time, the enzyme activity was inactivated for 10 min at 100° C. The gluten content of the solutions was determined by the process as described in Example 1. FIG. 2c shows the content of detectable gliadins as a function of incubation temperature.

3) Preparation of a Gliadin-Free Beer

Experiments were performed according to s standard brewing process. Ten kg of malt was crushed and brought to mashing temperature with 40 l of brewing water. After a typical mashing process with 40 l of sparge liquor, lautering was effected up to a volume of 75 l of wort. The subsequent boiling of the wort was effected for 60 to 90 minutes with hopping and a subsequent whirlpool rest period of 20 to 30 minutes. This was followed by coarse sludge separation, and the wort was cooled down to a pitching temperature of 6° C. by means of a plate cooler. For fermentation, bottom-fermenting yeast for pilsener type beers was used. The fermentation was effected over 6 days in tanks. Subsequently, the yeast was separated from the green beer, which was siphoned into Cornelius tanks for post fermentation and storage. After 20 to 30 days, the beers were filtered, bottled and pasteurized.

Figure 3:
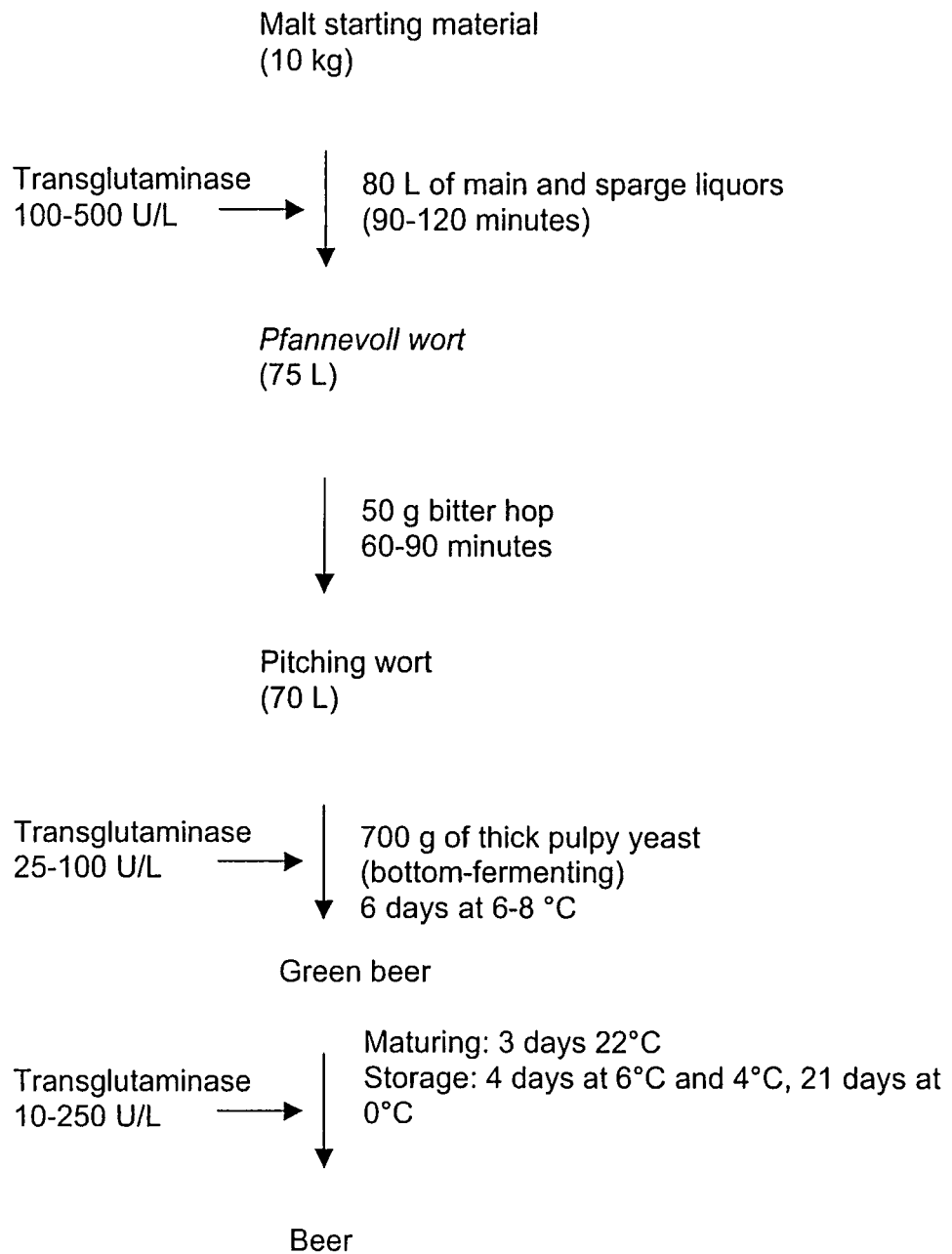
FIG. 3 shows a scheme relating to possible additions of transglutaminase during beer production.

3a) Action of Transglutaminase on Different Intermediate Products During the Brewing Process FIG. 3 schematically illustrates the brewing process for a beer of the pilsener type and illustratively shows the application of transglutaminase within different process steps.

3b) Action of Transglutaminase on Different Commercial Beers

Since wheat malt is also used for the preparation of Weizenbier in addition to barley malt, the beers prepared therefrom have a very high gluten content, which may often reach values of clearly >1000 ppm. Table 1 shows examples of the application of transglutaminase for the removal of gliadin in different commercially available beers. In the treated beers, no gliadins could be detected any longer after 24 hours of treatment at room temperature.

| Beer | Type | Gluten concentration [ppm] |
| --- | --- | --- |
| 1 | Weizenbier, light | 1500 |
| 2 | Weizenbier, light | 1725 |
| 3 | Weizenbier, dark | 360 |
| 4 | Pilsener | 170 |
| 5 | Pilsener | 590 |
| 6 | Pilsener, non-alcoholic | 40 |

4) Preparation of a Gliadin-Free Malt Base for Beverage Bases

In 1 l of warm water, 30 g of malt extract having a dry matter content of 80 Brix is solubilized at 40 to 50° C. with vigorous stirring. Subsequently, 100 to 1000 U of transglutaminase per l of the mixture is added, and all is stirred at 50° C. for 1 h. Insoluble components are subsequently removed by filtration or separation. The gliadin-free malt base can be formulated into a base with raw products usual in the beverage industry (e.g., juice, emulsions, stabilizers, acids, carbohydrates, flavors, essences, colorants, sugar substitutes) and ingredients (minerals, vitamins, functional ingredients) and with the use of known processing steps, such as homogenization and pasteurization.

5) Preparation of a Gliadin-Free Beverage

For the preparation of a gliadin-free malt beverage, the malt base treated according to the invention according to Example 4 is admixed with 0.3% lemon essence, 0.4% citric acid and about 8% sugar, bottled and subjected to a pasteurization step.

The invention claimed is:

1. A process for the preparation of a beverage having reduced prolamin content from prolamin-containing raw materials, comprising the following steps:
   a) providing a prolamin-containing beverage selected from the group consisting of a beverage produced from a malt, a beverage produced from a wort prepared from a malt, a beverage produced from a malt extract, and any combinations thereof;
   b) contacting said beverage with a transglutaminase cross-linking enzyme to obtain a modified prolamin in said beverage; and
   c) removing the modified prolamin from said beverage to produce said beverage having a reduced prolamin content.

2. The process according to claim 1, wherein said cross-linking enzyme comprises bacterial transglutaminase.

3. The process according to claim 1, wherein the prolamin-containing raw material comprises cereals selected from the group consisting of wheat, rye, oat, barley, spelt, unripe spelt grain, einkorn, emmer, triticale, bulgur, kamut, or any combinations thereof.

4. The process according to claim 1, wherein said beverage having reduced prolamin content is selected from the group consisting of alcoholic beer, alcohol-reduced beer, non-alcoholic beer, malt beer, beer mix beverages, emulsion beverages, dietetic beverages having a cereal content, or any combinations thereof.

5. The process according to claim 1, further comprising adding proteins and protein hydrolysates approved for foods to the beverage before, during or after said contacting with said cross-linking enzyme.

6. The process according to claim 1, wherein said removing is performed by a separation process.

7. The process according to claim 1, wherein said contacting is effected by the addition of a microorganism and/or a cereal, and wherein said microorganism or cereal recombinantly produces said cross-linking enzyme.

8. The process according to claim 7, wherein said microorganism is a yeast.

9. The process according to claim 1, wherein inactivation of said cross-linking enzyme is effected after said contacting.

10. The process according to claim 2, wherein said bacterial transglutaminase comprises $Ca^{2+}$-independent transglutaminase from *Streptoverticillium mobaraense*.

11. The process according to claim 5, wherein said proteins and protein hydrolysates are selected from the group consisting of gelatin, milk, whey proteins, and any combinations thereof.

12. The process according to claim 6, wherein said separation process is selected from the group consisting of filtration, centrifugation, sedimentation, sifting, and combinations thereof.

13. The process according to claim 9, wherein said inactivation is effected by heat treatment.

14. The process according to claim 1, further comprising malting said prolamin-containing raw material to form said malt.

15. A process for reducing prolamin content in a beverage precursor, comprising:
   a) providing a prolamin-containing beverage precursor selected from the group consisting of malt, wort prepared from a malt, malt extract, and any combinations thereof;
   b) contacting said beverage precursor with a transglutaminase cross-linking enzyme to obtain a modified prolamin in said beverage; and
   c) removing the modified prolamin formed in step (b) to produce a reduced-prolamin beverage precursor.

* * * * *